United States Patent [19]

Servais et al.

[11] Patent Number: 6,057,097
[45] Date of Patent: May 2, 2000

[54] MARKER FOR PATHOLOGIES COMPRISING AN AUTO-IMMUNE REACTION AND/OR FOR INFLAMMATORY DISEASES

[75] Inventors: Genevieve Servais, Horrues; Jean Duchateau, Brussels, both of Belgium

[73] Assignee: Universite Libre de Bruxelles, Brussels, Belgium

[21] Appl. No.: 08/666,562

[22] PCT Filed: Oct. 30, 1995

[86] PCT No.: PCT/BE95/00100

§ 371 Date: Oct. 28, 1996

§ 102(e) Date: Oct. 28, 1996

[87] PCT Pub. No.: WO96/13723

PCT Pub. Date: May 9, 1996

[30] Foreign Application Priority Data

Oct. 28, 1994 [BE] Belgium .................................. 9400985

[51] Int. Cl.$^7$ .......................... C12Q 1/68; G01N 33/567; G01N 33/53; C07K 16/28
[52] U.S. Cl. ........................... 435/6; 435/7.21; 435/7.24; 435/7.25; 435/7.94; 435/7.95; 435/975; 436/508; 436/811; 530/387.2; 530/388.21; 530/389.1; 536/23.1
[58] Field of Search ............................. 435/6, 7.21, 7.84, 435/7.25, 7.94, 7.95, 975; 530/387.2, 388.21, 389.1; 536/23.1; 436/505, 811

[56] References Cited

PUBLICATIONS

Meinke, W and Goldstein, DA. J. Mol. Biol. 86: 757–773, 1974.
Chan, TM et al. Clin. Exp. Immunol. 91: 110–114, Jan. 1993.
Halpern, R et al. J. Immunol. 133(4): 1852–1856, Oct. 1984.
Rieber, M et al. Biochem. Biophys Res. Comm. 159(3): 1441–1447, Mar. 31, 1989.
Harlow, E and Lane, D. in Antibodies: A Laboratory Manual. Harlow & Lane, eds. Cold Spring Harbor Laboratory, Cold Spring Harbor, NY. pp. 186–187, 1988.

*Primary Examiner*—David Saunders
*Assistant Examiner*—F. Pierre VanderVegt
*Attorney, Agent, or Firm*—Knobbe, Martens, Olson & Bear, LLP

[57] ABSTRACT

The present invention comprises a marker for inflammatory diseases and/or pathologies comprising an autoimmune reaction, which is the plasmatic membrane and/or a portion therof, in particular the plasmatic DNA. The present invention concerns also the method to obtain said marker and the diagnostic device which comprises said marker.

15 Claims, 1 Drawing Sheet

MARKER FOR PATHOLOGIES COMPRISING AN AUTO-IMMUNE REACTION AND/OR FOR INFLAMMATORY DISEASES

This is the U.S. national phase under 36 U.S.C. §371 of International Application PCT/BE95/00100, filed Oct. 30, 1995.

FIELD OF THE INVENTION

The present invention relates to a marker for pathologies comprising an auto-immune reaction and/or for inflammatory diseases, the antibodies directed against said marker and the antibodies directed against said antibodies.

The present invention relates also to a diagnostic device which comprises said marker and/or said antibodies.

The present invention also relates to a method for obtaining the marker present in an animal cell.

BACKGROUND OF THE INVENTION

Numerous pathologies comprising an auto-immune reaction and inflammatory diseases have an uncertain or unknown etiology and may have a multifactor origin.

Apparently, a disorder or a stimulation of the immune system of patients constitutes an important element of the progression of those diseases or pathologies.

Among the auto-immune diseases, systemic lupus erythematosus disease (SLE) is characterized by numerous biological and clinical signs.

However, SLE is a pathology with several clinical signs which may evolve and/or recover themselves each other (i.e. renal, cardiac, brain damages, . . . ). Therefore, as it exists non common and constant signs for all the patients affected by SLE, it has been proposed that the "diagnostic" of this pathology is now obtained from simultaneous characterization of at least four clinical and/or biological signs related to SLE (Arthritis and Rheumatism, Vol. 25, No 11 (1982), Official Journal of the American Rheumatism Association Section of the Arthritis Foundation).

The table 1 represents the sensitivity and the specificity of several preliminary criteria used for the diagnostic of systemic lupus erythematosus (serological and clinical tests).

TABLE 1

Comparison of sensitivity and specificity of elements in the 1982 and 1971 patient database

| Element | Sensitivity[1] 1982 | 1971 | Specificity[2] 1982 | 1971 |
|---|---|---|---|---|
| Malar rash | 101/177 (57) | (64) | 156/162 (96) | (98) |
| Discoid rash | 31/177 (18) | (17) | 161/162 (99) | (99) |
| Alopecia | 99/177 (56) | (43) | 143/162 (88) | (97) |
| Photosensitivity | 76/176 (43) | (37) | 155/162 (96) | (99) |
| Oral ulcers | 47/177 (27) | (15) | 155/162 (96) | (99) |
| Raynaud's | 51/176 (29) | (20) | 132/162 (81) | (99) |
| Arthritis | 152/177 (86) | (86) | 60/162 (37) | NA[3] |
| Proteinuria | 89/177 (50) | (61) | 148/157 (94) | (82) |
| Urinary casts | 64/176 (36) | (48) | 152/157 (97) | (89) |
| Dementia | 11/177 (6) | NA | 160/162 (99) | NA |
| Seizures | 21/177 (12) | (13) | 160/162 (99) | (98) |
| Coma | 8/177 (5) | NA | 162/162 (100) | NA |
| Psychosis | 22/176 (13) | (19) | 161/162 (99) | (95) |
| Focal neurologic | 21/177 (12) | (11) | 155/161 (96) | (92) |
| Pleurisy | 92/177 (52) | (60) | 144/162 (89) | (91) |
| Pericarditis | 31/177 (18) | (19) | 155/162 (96) | (97) |

TABLE 1-continued

Comparison of sensitivity and specificity of elements in the 1982 and 1971 patient database

| Element | Sensitivity[1] 1982 | 1971 | Specificity[2] 1982 | 1971 |
|---|---|---|---|---|
| Haemolytic anaemia | 31/176 (18) | (16) | 160/161 (99) | (98) |
| Leucopenia | 82/177 (46) | (40) | 144/161 (89) | (94) |
| Thrombocytopenia | 37/177 (21) | (11) | 160/161 (99) | (98) |
| LE cells | 58/79 (73) | (92) | 46/48 (96) | (98) |
| Sm antibody | 34/108 (31) | NA | 59/62 (95) | NA |
| Serologic test for syphilis | 19/129 (15) | (12) | 80/80 (100) | (99) |
| Renal biopsy | 57/69 (83) | NA | 10/10 (100) | NA |
| Skin biopsy | 47/69 (68) | NA | 13/16 (81) | NA |
| Antinuclear antibody | 174/175 (99) | NA | 68/139 (49) | NA |
| DNA antibody | 113/168 (67) | NA | 84/91 (92) | NA |
| CH50 | 84/120 (70) | NA | 33/47 (70) | NA |
| C3 | 88/137 (64) | NA | 69/76 (91) | NA |
| C4 | 65/102 (64) | NA | 33/51 (65) | NA |
| C2 | 0/0 | NA | 0/0 | NA |

[1]: Sensitivity was determined on the SLE population and is expressed as the number of patients who were positive over the number of patients in whom the test was determined. Number in parenthesis indicates percentage.
[2]: Specificity was determined on the control population and is expressed as the number of patients who were negative or normal over the number of patients in whom the test was determined.
[3]: NA = data non available State of the Art However, in order to improve the diagnostic of said pathology, efforts have been made to develop specific and reliable detection devices on the basis of clinical biology analysis.

The presently used techniques are based on the detection in the serum of anti-nuclear antibodies (ANA) directed against the autologous components present in the cell nucleus. The presence of those anti-nuclear components is associated to clinical manifestations of some auto-immune diseases.

The detection of those antibodies is generally effected previously to other tests for confirming the existence of an auto-immune disease.

The anti-nuclear auto-antibodies (ANA) can be divided into two subgroups, the anti-DNA auto-antibodies and the anti-ENA auto-antibodies (extractable nuclear antigens).

A better characterization of those anti-nuclear auto-antibodies (ANA) would allow to obtain a more detailed diagnostic on the auto-immune disease type.

Moreover, it has been shown that sera of SLE-affected patients contain a mixture of antibodies respectively able to react not only with nuclear DNA, but also with RNA and nucleoproteins. Besides, some patients presenting clinical signs of Systemic lupus erythematosus (SLE) have no significant titers of anti-DNA antibodies.

Consequently, it has not been shown yet that the presence of such antibodies in patients can be considered as a characteristic SLE marker.

In the European Patent EP-0252787 granted to Institut Pasteur and INSERM, a composition of isolated and purified cell surface polypeptides and the application thereof for detecting SLE are described. These purified polypeptides are characterised by a molecular weight less than 60 KD (55 KD, 43 KD, 34 KD, 33 KD, 17 KD, 16 KD and 14 KD).

However, for the inflammatory diseases and the pathologies comprising an auto-immune reaction, particularly for SLE, it has not been yet possible to provide a sufficiently specific antigenic structure to obtain a reliable diagnostic (in specificity and in sensitivity) for those pathologies and diseases.

Aims of the Invention

The present invention aims to provide a marker and a diagnostic device allowing to improve the diagnostic for inflammatory diseases and/or pathologies comprising an auto-immune reaction, particularly for SLE and/or Sjögren Syndrom.

A further aim is to provide a marker which improves the specificity and sensibility of SLE diagnostic, preferably an early diagnostic of SLE.

Another aim of the invention is to provide a method to obtain the marker, particularly a nucleic acid according to the invention.

A further aim of the invention is to provide an easy and reproducible method to obtain said marker in high amounts.

SUMMARY OF THE INVENTION

The present invention relates to a marker for inflammatory diseases and/or pathologies comprising an auto-immune reaction; said marker is the plasmatic membrane and/or a portion thereof having a molecular weight higher than 60 KD, preferably higher than 100 KD, both obtained from an animal cell containing molecular DNA (cmDNA).

Advantageously, said animal cell is a human blood cell, preferably a lymphoblastoid B, such as a Wil 2 cell.

It is meant by "pathology comprising an auto-immune reaction" auto-immune diseases and/or infections leading to a disorder of the immune system.

Auto-immunity is a an immunization state of a subject against its own constituents. Production by an organism of antibodies directed against its own constituents has been observed in a number of pathologies such as SLE affections, Gougerot-Sjögren syndrome (or Sjögren syndrome pathology), rheumatoid polyarthritis, etc. It is obvious that the expression "pathology comprising an auto-immune reaction" is in no way limited to those diseases, but also includes other pathologies such as sarcoidosis and osteopenia, spondylarthritis, scleroderma, multiple sclerosis, amyotrophic lateral sclerosis, hyperthyroidism, Addison's disease, auto-immune haemolytic anaemia, Crohn's disease, Goodpasture's syndrome, Graves' disease, Hashimoto's thyroiditis, idiopathic purpura haemorrhagica, insulin-dependent diabetes, myasthenia, pemphigus vulgaris, pernicious anaemia, poststreptococcal glomerulonephritis, psoriasis, scleroderma and spontaneous sterility.

It is meant by "a portion of the plasmatic cell membrane", any fragment obtained from said plasmatic cell membrane and having a molecular weight higher than 60 KD, preferably higher than 100 KD.

Said portion (or epitope) may be any constituent of said plasmatic membrane which can bind one or more antibodies present in the serum of a patient affected by an inflammatory disease and/or a pathology comprising an auto-immune reaction.

Advantageously, said fragment is a nucleic acid, preferably a DNA, which has a molecular weight higher than 60 KD, preferably higher than 100 KD.

The nucleic acid present in said plasmatic cell membrane has been previously described by Lerner et al. (Proc. Nat. Acad. Sci. U.S.A., Vol. 68, No 6, pp. 1212–1216 (1971)).

According to Lerner et al., said specific DNA is not a viral, a mycoplasmic, a mitochondrial or a nuclear nucleic acid.

The Inventors have discovered that the nucleic acid they have isolated is from the plasmatic membrane not coming from apoptotic cells (the electrophoresis obtained does not correspond to the electrophoresis of a nuclear DNA).

Said DNA does not correspond to a mitochondrial DNA as the $ORF_1$ and $ORF_4$ probes cannot hybridize to the DNA according to the invention.

As the viability of the Wil 2 cell is comprised between 95 and 98%, said DNA cannot come from nuclear DNA of dead cell absorbed on the surface or the Wil 2 cell.

According to Kuo et al. (Proc. Nat. Acad. Sci. U.S.A., Vol. 72, pp. 5004–5006 (1975)), said specific DNA is probably of chromosomal origin (chromosome 9) and according to Meinke et al. (J. of Molecular Biology, Vol. 78, pp. 43–56 (1973)), said DNA has been also isolated from hepatic and other lymphoid cells.

Other characteristics of said DNA (synthesis, localisation, physicochemical properties, . . . ) were described by Hall et al. (Nature New Biology, Vol. 234, pp. 227–229 (1971)).

The Inventors have also demonstrated that the antibodies directed against said DNA are different from the anti-nuclear auto-antibodies (ANA). Bennet et al. (J. of Clin. Invest., Vol. 71, pp. 611–618 (1983), J. Rheumatol., Vol. 13, pp. 679–685 (1986) and Clin. Exp. Immunol., Vol. 86, pp. 374–379 (1991)) have not been able to confirm that the anti-nuclear auto-antibodies (ANA) were able to bind the DNA obtained from the membrane of human blood cells.

The results of Bennet et al. have been confirmed by Kubota et al. (Immunology Letters, Vol. 23, pp. 187–194 (1990)). Kubota et al. have identified upon the membrane, histone which is involved in the cross-reactivity of some anti-nuclear auto-antibodies (ANA) against the membrane of lymphocyte B cell line (Raji).

Therefore, said histone may bind exogenous DNA (Emlem et al., J. Immunol., Vol. 148, pp. 3042–3048 (1992)).

These results have been also confirmed by Muso and Jacob (Clin. Immunol. and Immunopathol., Vol. 42, pp. 370–374 (1987)). Muso and Jacob have identified the protein which is able to bind the histone DNA complex (Jacob et al., Proceeding of National Academy of Sciences USA, Vol. 86, pp. 4669–4673 (1989)).

Hereafter, the Inventors demonstrate that it is possible to obtain auto-antibodies purified from the serum of patients affected with SLE. Said auto-antibodies are obtained from a chromatographic process wherein a cmDNA obtained from Wil 2 cells is fixed on a solid support in a chromatographic process. Said auto-antibodies are specific for SLE and may bind the DNA according to the invention in a ELISA test or in immunofluorescence.

The Inventors have also demonstrated that these antibodies are different from the anti-nuclear auto-antibodies (ANA).

The present invention is also related to the antibodies (polyclonal or monoclonal) or a portion thereof directed against said marker and to the antibodies (polyclonal or monoclonal) or a portion thereof directed against said antibodies anti-marker.

The term "a portion thereof" means a fragment of said antibodies (such as the $Fab'_2$ portion) which is able to bind specifically the marker or the antibodies according to the invention.

The present invention is also related to a diagnostic device, such as a kit or a chromatographic column, which comprises the marker and/or the antibodies or a portion thereof according to the invention.

Preferably, the diagnostic device also comprises the reactants for detection and/or dosage of antibodies or nucleotides sequences through a method selected from the group consisting in the in situ hybridization, hybridization or recognition by marked antibodies such as ELISA (Enzyme Linked Immunosorbent Assay) or RIA (Radio Immunoassay) method on filter, on a solid support, in solution, in "sandwich", on gel, Dot blot hybridization, Northern blot hybridization, Southern blot hybridization, by an isotonic or non-isotopic labelling (such as immunofluorescence or biotynilation), by a technique of cold probes, by genetic amplification, particularly PCR or LCR, by a double immunodiffusion, by a counter-immunoelectrophoresis, by haemagglutination, by enzyme conjugation and/or a mixture thereof.

Another aspect of the present invention relates to a method for obtaining the marker according to the invention wherein the plasmatic membrane is isolated from animal cells, preferably from human blood cells, particularly from lymphoblastoids B, such as the Wil 2 cells.

Advantageously, the membrane is isolated from the animal cell through its fixation upon a solid support by the addition of an organic solvent.

Preferably, said method comprises also the further steps, wherein the isolated membrane is treated by an enzyme selected from the group consisting of RNase, DNase, pronase (or peptidase) lipase, glycosidase and/or a mixture thereof, and wherein the marker obtained is recovered.

The present invention is also related to a process for the detection in vitro or antibodies related to inflammatory diseases and/or pathologies comprising an auto-immune reaction, preferably systemic lupus erythematosus and/or Sjögren, in a biological fluid containing said antibodies, the process comprising the following steps:

the biological fluid, preferably a serum, is put in contact with the marker according the invention or to a marker obtained by the method according to the invention and/or to an antibody or portion thereof directing against the antibodies (directed against the marker according to the invention), in order to obtain an immunological binding in vitro between the antibody present in the biological fluid and said marker or said antibody, and detection in vitro of the binding obtained.

EXAMPLES

Materials

1. Cell Lines

Figure 1:
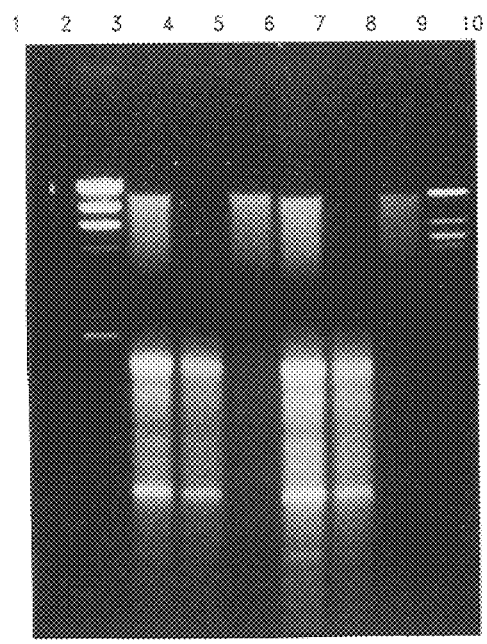
FIGS. 1 and 2 show electrophoresis gels of the human membranous double-stranded DNA possibly preincubated with specific haemoglobulins (IgG) of SLE having undergone various treatments, The invention will be further described in the following non limiting examples.

The cell lines of human lymphoblastoids B (Wil 2 NS) obtained from ICN Flow Laboratories (ECACC No 90112121) are maintained in RPMI 1640 added with 10% foetal calf serum (heat inactivated and tested for the absence of mycoplasmas), L Glutamine and 40 µg/ml Gentamycine, humid oven at 37° C. and 5% $CO_2$. Cells are removed in the growing logarithmic phase corresponding to a cell density of 1–1,2 $10^6$ cells/ml and showing a Trypan Blue exclusion of more than 95%.

2. Sera

The sera are obtained from patients affected by several inflammatory diseases or pathologies having an auto-immune reaction and from normal individuals. The sera are obtained from centrifuged coagulated blood and held at −20° C. until use.

Methods

1. Indirect Immunofluorescence on Cells 1.1. Immunofluorescence on Methanol Fixed Cells Wil 2 cells are washed twice with Hank's solution (Gibco BRL) and resuspended at $0.5 \times 10^6$/ml and subsequently spotted on glass slides divided into 20 µl wells.

After drying at 37° C. in an oven, the cells are fixed for 3 min. in methanol and washed once in PBS (Phosphate Buffered Saline, 10 mM pH 7.4). The cells are then incubated for 30 min. at room temperature in the presence of goat IgG (Fc fraction, Organon Technica) at 6 µg/well in 20 µl PBS, then washed in PBS. They are then incubated for 25 min. at room temperature in the presence of different dilutions of patients or control sera at 20 µl/well and washed again in PBS. In some experiments, as noted, an IgG fraction is used instead of whole sera.

The slides are further incubated for 30 min. in the presence of 20 µl of fluorescein-conjugated goat anti-human IgG (Kallestadt) diluted 1/50 in PBS.

A final wash of the slides is performed with PBS alone, followed by PBS containing Evans Blue as counterstain.

Finally, slides are mounted in glycerin/PBS (2:1), pH 9, and visualized by means of a UV immersion microscope (Leitz Orthoplan), magnification=10×40).

Scoring of the patterns observed were as follow:

a negative results ("0") corresponds to the absence of any membrane fluorescence, a cell membrane punctate pattern is arbitrarily referred as "1", and a cell membrane peripheral continuous ring is scored as "2".

1.2. Immunofluorescence on Non-fixed Cells

The reactions are performed on cells suspensions at 4° C. to reduce receptor turnover and internalization. Briefly, cells ($1 \times 10^6$) in 1 ml of culture medium are placed in plastic (5 ml) tubes and washed with PBS containing 10 mM EDTA and 0.01% Na azide (PBS EA) by centrifugation (500×g, 10 min.).

The pellet is resuspended with 600 µg of goat IgG in 900 µl of the same buffer and incubated for 30 min. at 4° C.

Subsequently, cells are washed twice in the same buffer as above. Sera or purified IgG for either patients or controls are incubated at different dilutions with the cells for 30 min. at 4° C. A new washing cycle is performed, followed by incubation with fluorescein-conjugated goat anti-human IgG (Kallestadt), diluted 1/50 in 200 µl of PBS EA.

Four washes are performed in the same conditions as described above, and the cell pellet is resuspended in PBS EA containing Evans Blue as counterstain. 10 µl of this cell suspension are placed onto a glass slide, covered and visualized by UV microscopy.

1.3. DNase, RNase and Pronase Treatment of Cells

After methanol fixation of the slides, DNase RQ1®, RNase free (Promega) is incubated (20 µg in 20 µl of PBS) with the cells for 60 min. at room temperature. The RNase treatment (RNase I®, Promega; 2 µg in 20 µl of PBS) is also performed for 60 min. but at 37° C.

After two washings of the slides in PBS, the subsequent steps of the procedure are performed as described above.

The pronase treatment (10 µl from sigma) was performed for 1 hour at 37° C. The subsequent steps of the procedure are performed as described above.

2. ELISA Upon Isolated Membrane from Wil 2 Cells

The Wil 2 cells membranes are obtained according to the method described by Bennet et al. (J. Clin. Invest., Vol. 71, pp. 611–618 (1983)).

3.1. DNA (cmDNA) Isolated from Wil 2 Cells Membrane

1×109 cells Wil 2 are pooled together into two tubes from said pellets re-suspended in a PES buffer (10 mM salt phosphate buffer, pH 7.2) and washed with 50 ml of the same buffer (500×g, 10 minutes). Two other washings are then carried out with 50 ml per tube of RBS buffer (1 ml HCl 1M, 0.2 ml NaCl 5M, 0.2 ml $MgCl_2$ 1M extended up to one liter with distilled water). Each pellet obtained is re-suspended in 10 ml RBS and 30 µl $NP_4O$ are added to each tube. After an incubation of 10 minutes at room temperature, the tubes are centrifuged at 2000×g during 4 minutes. The supernatants are submitted to centrifugation with same conditions and after a transfer into new tubes (the following elements being added to each supernatant: 0.32 ml EDTA 0,5M, 3.2 ml NaCl 5M, 1 ml 10% SDS), the volume in each tube is adjusted to 16.7 ml.

After an overnight incubation at 4° C., the supernatants of a centrifugation (20000×g, 30 minutes, 4° C.) are extracted twice with phenol and extracted with chloroform: isoamyl alcohol (24:1). A 3 min centrifugation at 2000×g is carried out between each step to separate the phases. Two volumes of absolute ethanol are added per volume of the aqueous phase obtained. After an overnight incubation at 4° C. and a 30 min centrifugation at 20000×g, the pellet is re-suspended in 0.2 ml TE buffer (Tris 10 mM, EDTA 1 mM, pH 8).

An electrophoresis on 1% agarose of the resulting product shows an DNA band of ±17000 base pairs and two slighter RNA bands (corresponding to ±2000 and 1000 pairs of bases).

The use of those cell lineages of lymphoblastoids B makes possible to obtain easily a human-specific "antigenic" structure.

3.2. Enzymatic Treatment of Said Purified DNA (cmDNA)

However, as that structure can be formed with DNA associated with RNA and proteins, an one hour digestion is carried out at 37° C. with RNase I® provided by Promega.

To 100 µl of the preparation, 50 U/5 µl RNase and 25 ml buffer 10 mM Tris HCl, 5 mM EDTA, 200 mM sodium acetate, pH 7.5, are added. The reaction is stopped by addition of 10 µl NaCl 5M.

A new phenol extraction is then carried out to remove the enzyme and the preparation is passed through a column of 1 ml Sephadex G50 ("spun column") so as to remove the oligonucleotides resulting from the RNA digestion.

Another digestion with pronase is carried out to confirm the absence of protein traces associated with the membrane DNA.

To 100 µl of the product digested by the RNase 5 µg/10 µl pronase are added during 1 hour at 37° C.

Two extractions with phenol followed by an extraction with chloroform: isoamyl alcohol (24:4) are then carried out and the aqueous phase is sent through Sephadex G50. An electrophoresis on 1% agarose is carried out to confirm the so obtained membrane DNA size.

By comparing with the size of the DNA fragments digested by HindIII, the membrane DNA size is estimated to ±17000 pairs of bases.

The membrane DNA is then considered as being pure, that means advantageously free of contaminants such as RNA or proteins which can interfere in the recognition phenomenon with antibodies directed against RNA.

3.3. ELISA Upon the Isolated DNA (cmDNA) Treated or not by Enzymes

The Wells of a microplate "IMMUNOPLATE MAX-ISORB®" (NUNC) are coated with 100 µl poly-L-Lysine (10 µg/ml) during 2 hours at 37° C.

Then, 100 µl purified membrane DNA, digested by RNase and pronase (15 mg/ml), are incubated in wells for 3 hours at 37° C.

A saturation of the Wells is carried out through incubation of a solution of 10% horse serum supplied by Pharmacia in a buffer PBS (150 µl/wells, 2 hours, 37° C.).

The serum of lupus-affected or control patients (blood donors) is then incubated in the wells in series dilutions (100 µl of the dilutions from 1/20 to 1/1280 in buffer PBS) overnight at room temperature.

100 µl of rabbit immunoglobulines (IgG) directed against the human immunoglobulines (IgG) and conjugated with peroxidase (DAKO), 1/250 diluted in buffer PBS, are added to each well during 2 hours at 37° C.

The last step is a calorimetric reaction formed with the "substrate" solution (30 µl $H_2O_2$) (Perhydrol®, Merck) and 17.5 mg orthophenylene diamine in 20 ml buffer PBS).

A washing of the cupules is carried out between each step by buffer PBS.

Results

1. Purified DNA (cmDNA) from Wil 2 Membranes

Figure 2:
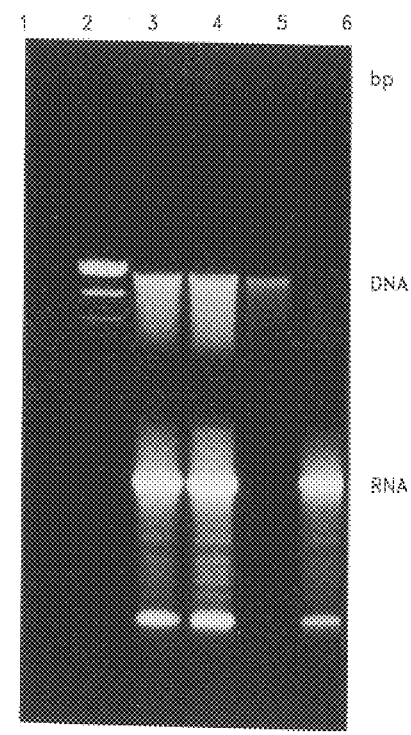

The FIGS. 1 and 2 show pictures of electrophoresis gels of the resulting preparations (possibly incubated with lupus-specific immunoglobulines at different dilutions) and treated with different enzymes, particularly phospholipase, pronase, RNase and DNase. The resulting products are compared to DNA size markers.

The FIG. 2 shows that the raw preparation contains a few proteins removed by pronase (column 4), but it is possible to obtain an RNA-free pure product (column 5).

Column 6 clearly shows that the resulting active product is constituted by DNA.

Other production methods can be used to obtain a contaminant-free human membranous nucleic acid, particularly DNA.

It is particularly possible to obtain special derivatives of said nucleic acid, such as fragments or epitopes of said nucleic acid.

A purification process can include an affinity chromatography using specific antibodies directed against all or part of that nucleic acid bound to a solid phase.

Said nucleic acid or fragments thereof can be also purified by electrophoresis on a convenient gel.

The antibodies directed against said nucleic acids and the antibodies directed against said antibodies can be obtained by immunization of animals and produced in high amounts through selection of particular hybridomes.

2. Effect of the Preincubation of Immunoglobulines (IgG) from Lupus-affected or Healthy Patients with the Purified Membrane DNA on its Migration on Agarose Gel As shown by the picture of the FIG. 1, the preincubation of membrane DNA with the various dilutions of purified immunoglobulines (IgG) from serum of a lupus-affected patient, shows a migration delay proportional to the added IgG quantity.

The digestion of this mixture by pronase cancels or reduces strongly that delay. In opposition, the same experience made with the same quantities of purified immunoglobulines (IgG) from a serum of a blood donor shows no effect on the electrophoretic migration of membrane DNA.

3. Effect of the Predigestion of Cells with RNase or DNase on the Binding of the IgGs from Lupus-affected Patients to Plasma Membranes of Cells Wil 2

Table 2 represents the percentage of fluorescent cells giving each images ("0"=no fluorescence, "1"=point membranous fluorescence, "2"=continuous membranous fluorescence). The given values are the arethmetic average results of 6 experiments.

Cell treatment with DNase gives for sera of patients 1, 2, 6 a reduction of the cell percentage giving an image "2", whereas, for the sera of patients 3, 4, 5, there is shown either no enzyme effect or even an increase of the cell percentage "2".

That could be due to the fact that the fluorescence image groups together various recognized specificities on the membrane of cells Will 2, which specificities include membrane DNA.

Treatment with RNase causes per se an increase of the cell percentage giving image "2", suggesting that RNA, maybe associated with membrane DNA, could partly mask the specific sites for those antibodies.

4. Fluorescence Obtained on Membranes of Cells Wil 2 After Binding of Serum, IgG Fraction or Specific IgG Fraction of Membrane DNA Table 3 demonstrates that the serum fraction responsible for the fluorescent image is due to immunoglobulines (IgG). Moreover, the membrane DNA specific IgGs allow sometimes to obtain a fluorescent image. It is to be pointed out at that time that the membrane DNA specific IgGs are used at lower concentration than the total IgGs.

TABLE 2

Images observed by fluorescence further to serum incubation of lupus-affected patients on cells Wil 2

|  | "2" | "1" | "0" |
|---|---|---|---|
| Control | 0 | 0 | 100 |
| + DNase | 0 | 0 | 100 |
| + RNase | 0 | 96 | 4 |
| Patient SLE 1 | 86 | 21 | 3 |
| + DNase | 3 | 92 | 5 |
| + RNase | 94 | 3 | 3 |
| Patient SLE 2 | 59 | 23 | 18 |
| + DNase | 27 | 43 | 30 |
| + RNase | 65 | 18 | 17 |
| Patient SLE 3 | 11 | 20 | 79 |
| + DNase | 17 | 28 | 55 |
| + RNase | 53 | 35 | 30 |
| Patient SLE 4 | 19 | 25 | 56 |
| + DNase | 18 | 12 | 70 |
| + RNase | 31 | 33 | 36 |
| Patient SLE | 78 | 9 | 13 |
| + DNase | 79 | 4 | 17 |
| + RNase | 79 | 9 | 12 |
| Patient SLE 6 | 21 | 24 | 55 |
| + DNase | 6 | 22 | 72 |
| + RNase | 55 | 28 | 17 |
| Patient SLE 7 | 89 | 2 | 9 |
| + DNase | 1 | 15 | 24 |
| + RNase | 94 | 1 | 5 |

Notes:
image "0" = no fluorescence
image "1" = point membranous fluorescence
image "2" = continuous membranous fluorescence The first line of results corresponds to the average (on 6 experiments) of the cell number showing each fluorescent image. The second line (DNase) and the third line (RNase) show the percentage of those cells after a predigestion either with DNase or RNase.

TABLE 3

Immunofluorescence images due to binding to cells Wil 2 of serum, total IgGs or specific marker IgGs

| Serum, IgG or anti-marker IgG | Bound Cells | Unbound Cells |
|---|---|---|
| Control serum | 0 | 0 |
| IgG | 0 | 0 |
| Serum SLE 1 | 2 | 2 |
| IgG | 2 | 2 |
| IgG-marker | 1 | 1 + 2 |
| Serum SLE 2 | 2 | 2 |
| IgG | 2 | 2 |
| IgG-marker | 1 | 1 + 2 |
| Serum SLE 3 | 2 | 2 |
| IgG | 2 | 1 |
| IgG-marler | 0 | 0 |

This table shows the results of three different experiments.

TABLE 4

Results in fluorescence obtained from sera of patients with SLE upon three different epitopes obtained from the membrane of Wil 2 cells (in percentages).

| Image "2" | Image "1" | Image "0" |
|---|---|---|
| Epitope 1: Fixed cells | | |
| 86 | 21 | 3 |
| 59 | 23 | 18 |
| 11 | 20 | 79 |
| 19 | 25 | 56 |
| 78 | 9 | 13 |
| 21 | 24 | 55 |
| 89 | 2 | 9 |
| Average: 51 | Average: 17 | Average: 32 |
| Epitope 2: Fixed cells treated by DNase | | |
| 3 | 92 | 5 |
| 27 | 43 | 30 |
| 17 | 28 | 55 |
| 18 | 12 | 70 |
| 79 | 4 | 17 |
| 6 | 22 | 72 |
| 1 | 15 | 24 |
| Average: 23 | Average: 34 | Average: 42 |
| Epitope 3: Fixed cells treated by RNase | | |
| 94 | 3 | 3 |
| 65 | 18 | 17 |
| 53 | 35 | 30 |
| 31 | 33 | 36 |
| 79 | 9 | 12 |
| 55 | 28 | 17 |
| 94 | 1 | 5 |
| Average: 66 | Average: 18 | Average: 16 |

Image "2" for a seric dilution of 1/40

These results indicate that the enzymatic treatment of the membrane modifies its ability to bind the antibodies.

For the diagnostic of SLE, the immunofluorescence is characterized by a specificity of 100% and a sensibility of 43%, and for the detection of Sjögren syndrome, the sensibility is 3%.

5. Detection of Membrane Anti-DNA Antibodies by ELISA Technique in Different Auto-immune Diseases The physiological fluid (serum) of the following patients has been tested with the ELISA diagnostic device according to the invention:

68 lupus

34 Sjögren syndrome 15 ankylosing spondylarthritis 17 osteopenia 44 healthy donors 5.1. Characteristics of the ELISA Device Specificity:

The ELISA is specific, as, if auto-antibodies (IgGs) are purified by affinity and are added to a serum of a healthy donor, the optical density in ELISA changes from 0.241 to 0.898.

Sensitivity:

up to 16 AU/ml cc, which corresponds to a serum dilution of 1/3200 of a positive serum.

Reproducibility:

intra-assay:

CV<5% calculated on optical densities of the curve,

CV<6% calculated on arbitrary units (patient sera), inter-assay:

CV<10% calculated on arbitrary units (patient sera)

CV=10% on slopes of 4 standard curves obtained in 4 different assays at different days Positivity threshold:

69 AU/ml (average +2 sd of 44 donors)

5.2. Dosage of the Marker with ELISA Diagnostic Kit

By definition, the healthy donors do not have any anti-membrane IgG. Osteopenia-affected patients are negative, lupus-affected patients have high levels and Sjögren syndrome-affected patients have well higher levels than lupus.

A particularly high diagnostic is also observed with sarcoidosis-affected patients.

TABLE 5

| Total CmDNA | SLE | Sjögren | SPA | Sarcoidosis | Osteopenia | Healthy patients |
|---|---|---|---|---|---|---|
| cmDNA | 36/68 | 15/17 | 7/9 | 10/13 | 3/17 | 0/12 |
| without RNA and protein | 33/68 | 25/34 | 7/9 | 10/13 | 4/17 | 0/37 |
| cmDNA without RNA | 35/68 | 17/17 | 8/9 | 11/13 | 4/7 | 0/12 |
| cmDNA treated with DNase | 0/68 | 0/17 | 0/9 | 0/13 | 0/7 | 0/12 |

Therefore, it seems that the antigenicity of the marker is modified according to the enzymatic treatment of said marker.

In addition, the optical density measured with ELISA is modified when the marker (membrane) is modified by an enzymatic treatment.

TABLE 6

| Marker | Optical density |
|---|---|
| Non-treated membrane | 0.660 |
| Membrane treated with DNase | 0.508 |
| Membrane treated with RNase | 0.673 |

The following table 7 describes the dosage of membrane anti-DNA with ELISA diagnostic kit.

TABLE 7

| | Osteopenia | SLE | SPA | Sjögren syndrome | Sarcoidosis |
|---|---|---|---|---|---|
| Av. AU/ml | 54 | 102 | 136 | 176 | 178 |
| sd | 2 | 3 | 3 | 3 | 3 |

5.3. Correlation between the auto-antibodies calculated by ELISA and immunofluorescence on Wil 2 cells The levels by ELISA are correlated with the increase of the % of image "1" and "2" and a reduction of the negative image percentage "0".

| | Images obtained by immunofluorescence | | |
|---|---|---|---|
| ELISA | 0 | 1 | 2 |
| IgG < 69 AU | 123 | 15 | 2 |
| IgG > 69 AU | 87 | 22 | 10 |

Chi Squared 9.47 p=0.0088

Taking pathologies into account:

| ELISA | SLE | Sjögren syndrome | Osteopenia |
|---|---|---|---|
| IgG < 69 AU | 35 | 9 | 13 |
| IgG > 69 AU | 33 | 25 | 4 |

Chi Squared 49 p=0.00001

When ELISA levels and immunofluorescence images are related for different pathologies:

| | Healthy patients | SLE | | | Sjögren | | | Osteopenia |
|---|---|---|---|---|---|---|---|---|
| IF | 0 | 0 | 1 | 2 | 0 | 1 | 2 | 0 |
| ELISA < 69 AU | 37 | 22 | 11 | 2 | 9 | 0 | 0 | 13 |
| ELISA > 69 AU | 0 | 14 | 12 | 7 | 23 | 1 | 1 | 4 |

Chi Squared 55 p<0.00001

That means that in lupus the higher levels with ELISA are correlated with an image "2" whereas in Sjögren syndrome the higher levels with ELISA are correlated with an image "0".

5.4. Correlation Between Anti-marker (cmDNA) Auto-antibodies Levels with ELISA and Single- or Double-stranded Anti-nuclear DNA Antibodies (ANA) Levels with ELISA 262 sera were measured with 3≠ELISA and classified according to the level of their antibodies.

Distributions are different, as both assays do not measure the same antibody specificities.

| | | Membrane anti-cmDNA IgG with ELISA | |
|---|---|---|---|
| | | <69 AU/ml | >69 AU/ml |
| ANA IgG (DNA ds) with ELISA | < 40 AU/ml | 140 | 102 |
| | > 40 AU/ml | 3 | 17 |

-continued

| | Membrane anti-cmDNA IgG with ELISA | |
|---|---|---|
| | <69 AU/ml | >69 AU/ml |
| ANA IgG (DNA ss) with ELISA | < 40 AU/ml<br>> 40 AU/ml | 122<br>21 | 83<br>36 |

ANA IgG (DNA ds) with ELISA Squared chi 12.0 p<0.0005
ANA IgG (DNA ss) with ELISA Squared chi 8.35 p<0.004
Many sera of high anti-cmDNA IgG level are negative in ANA (DNA ds or ss).

6. Longitudinal Study of Lupus-affected Patients/Anti-cmDNA IgG with ELISA and by Immunofluorescence Compared to Anti-ANA (DNA ds and ss) with ELISA

| | Time in months | | | |
|---|---|---|---|---|
| | 0 | 6 | 8 | 10 |
| IF 1/40 | "2" | "2" | "2" | "2" |
| DNA ds | 338 | 225 | 398 | 262 |
| DNA ss | 347 | 262 | >400 | 386 |
| cmDNA | 362 | 72 | 170 | 78 |

| | Time in months | | | | | |
|---|---|---|---|---|---|---|
| | 0 | 1 | 2 | 4 | 5 | 6 |
| IF 1/40 | "0" | "0" | "1" | "0" | "0" | "1" |
| DNA ds | 5281 | 178 | 61 | 26 | 46 | 57 |
| DNA ss | 145 | 145 | 56 | 49 | 61 | 77 |
| cmDNA | 1651 | 228 | 55 | 186 | 203 | 55 |

DESCRIPTION OF FIGURES

FIG. 1

1. lambda HindIII markers
2. phospholipase digested mDNA
3. pronase digested mDNA
4. IgG lupus 1/20 preincubated mDNA
5. IgG lupus 1/20 preincubated mDNA, and then pronase digestion
6. IgG lupus 1/5 preincubated mDNA
7. IgG lupus 1/5 preincubated mDNA, and then pronase digestion
8. Ecori markers
9. DNase digested pure mDNA
10. RNase and pronase digested pure mDNA

FIG. 2

1. Void
2. HindIII
3. raw preparation
4. pronase digested raw preparation
5. RNase digested raw preparation
6. DNase digested raw preparation

We claim:

1. A diagnostic kit for inflammatory disease or pathology comprising an auto-immune reaction, comprising:
    an antibody specific for membranous DNA or an antigen-binding portion of an antibody specific for membranous DNA; and
    reactants for detecting said antibody or portion specific for membranous DNA.

2. The diagnostic kit according to claim 1, wherein said reactants for detecting said anti-membranous DNA antibodies functions in a method selected from the group consisting of in situ hybridization, hybridization, and recognition by marked specific antibodies, said method being conducted on filter, on solid support, in solution, or on gel, by using at least one technique selected from the group consisting of a sandwich method, Dot blot hybridization, isotopic or non-isotopic labelling, cold probe techniques, double immunodiffusion, counter-immunoelectrophoresis, and hemagglutination.

3. The diagnostic kit according to claim 1, wherein the animal cell is a human blood cell.

4. The diagnostic kit according to claim 3, wherein the human blood cell is a lymphoblastoid B cell.

5. The diagnostic kit according to claim 4, wherein said human blood cell is a Wil 2 cell.

6. A process for in vitro detection of an antibody related to inflammatory disease or pathology comprising an auto-immune reaction, comprising the following steps:
    (a) placing a biological fluid, in which said antibody may be present, in contact with at least either:
        a marker obtained from an animal cell, said marker being a plasmatic membrane containing a membranous DNA or being a portion of said membrane containing or consisting of a membranous DNA, said marker having a molecular weight higher than 60 kD
        or
        an anti-marker antibody or antigen-binding portion thereof specific for said membranous DNA
        in order to obtain either a biological binding in vitro between said antibody present in the biological fluid and said marker,
        or a competitive immunological binding in vitro between said antibody present in the biological fluid and said anti-marker antibody or said antigen-binding portion thereof specific for said membranous DNA; and
    (b) detecting in vitro the binding obtained.

7. A process according to claim 6, wherein the pathology comprising an auto-immune reaction is systemic lupus erythematosus or Sjögren syndrome.

8. A process according to claim 7, wherein said biological fluid is a serum of a patient having inflammatory disease or pathology comprising an auto-immune reaction.

9. The process according to claim 6, wherein the animal cell is a human lymphoblastoid B cell.

10. The process according to claim 9, wherein the human lymphoblastoid B cell is a Wil 2 cell.

11. The process according to claim 6, wherein said marker is membranous DNA.

12. The process according to claim 6, wherein the biological fluid is a serum.

13. A reagent set for identifying inflammatory disease or pathology comprising an auto-immune reaction, comprising:

a biological fluid from a patient suspected of having said inflammatory disease or pathology, said biological sample containing anti-membranous DNA antibodies when said inflammatory disease or pathology is present;

a marker obtained from an animal cell, said marker being a portion of a plasmatic membrane comprising or consisting of a membranous DNA, said marker having a molecular weight higher than 60 kD; and reactants for detecting said anti-membranous DNA antibodies bound to said marker.

14. The diagnostic kit according to claim 13, wherein said marker consists of said membranous DNA.

15. The diagnostic kit according to claim 13, wherein said portion is a lysed cell membrane.

* * * * *